(12) United States Patent
Frushour et al.

(10) Patent No.: US 9,974,524 B2
(45) Date of Patent: May 22, 2018

(54) THORACIC BIOPSY INSTRUMENT WITH BIPOLAR SEALING AND BLADE TECHNOLOGY

(71) Applicant: COVIDIEN LP, Mansfield, MA (US)

(72) Inventors: Scott E. M. Frushour, Boulder, CO (US); Anthony B. Ross, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 48 days.

(21) Appl. No.: 14/810,576

(22) Filed: Jul. 28, 2015

(65) Prior Publication Data

US 2016/0089123 A1 Mar. 31, 2016

Related U.S. Application Data

(60) Provisional application No. 62/055,413, filed on Sep. 25, 2014.

(51) Int. Cl.
| | | |
|---|---|---|
| *A61B 10/04* | (2006.01) | |
| *A61B 18/18* | (2006.01) | |
| *A61B 10/02* | (2006.01) | |
| *A61B 18/14* | (2006.01) | |

(52) U.S. Cl.
CPC .......... *A61B 10/04* (2013.01); *A61B 10/0266* (2013.01); *A61B 18/1442* (2013.01); *A61B 18/1815* (2013.01); *A61B 2018/1869* (2013.01)

(58) Field of Classification Search
None
See application file for complete search history.

(56) References Cited

U.S. PATENT DOCUMENTS 5,603,711 A * 2/1997 Parins .................... A61B 10/06
606/51

OTHER PUBLICATIONS

Weyant, Michael, et al., "VATS Mediastinal Nodal Dissection," VATS Mediastinal Nodal Dissection—CTSNet dated Tuesday, Jul. 1, 2008, retrieved Jan. 27, 2016, http://www.ctsnet.org/article/vats-mediastinal-nodal-dissection.

\* cited by examiner

*Primary Examiner* — Devin Henson
*Assistant Examiner* — Benjamin Melhus

(57) ABSTRACT

A biopsy instrument for removing nodes such as lymph nodes may include one or more of a blade for mechanical cutting of the ducts that connect the node to surrounding tissue and/or an energy emitter for emitting energy to seal the ducts and/or contribute to the gentle removal of the node from its connecting ducts. The biopsy instrument may include a ring clamp assembly made up of two opposing ring structures that may be clamped together such that the desired tissue sample (e.g., a lymph node) is captured within the inside opening of the clamped rings. Connecting ducts may be severed using either a blade or energy emitted from the ring clamps.

8 Claims, 15 Drawing Sheets

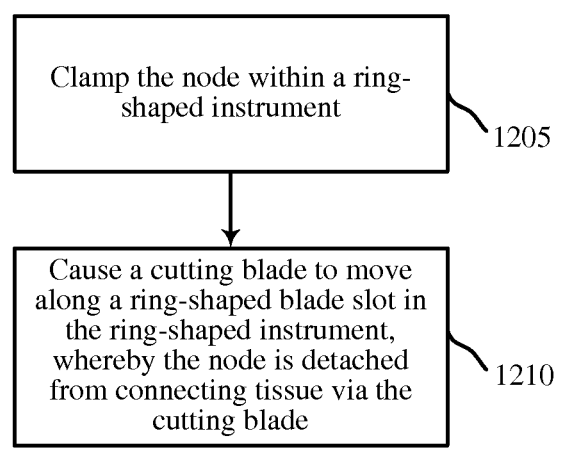

1400

THORACIC BIOPSY INSTRUMENT WITH BIPOLAR SEALING AND BLADE TECHNOLOGY

CROSS REFERENCE TO RELATED APPLICATION

The present application claims the benefit of and priority to U.S. Provisional Application Ser. No. 62/055,413, filed on Sep. 25, 2014, the entire contents of which are incorporated herein by reference.

BACKGROUND

The present disclosure relates generally to a biopsy instrument having a ring clamp assembly used for, for example, endoscopic surgical procedures. More particularly, the present disclosure relates to a biopsy instrument having a ring clamp assembly that may be used to both secure and remove a biopsy sample from surrounding tissue in a patient by using one or more of a mechanical blade technology and applied energy such as electrosurgical energy.

A biopsy procedure typically involves the removal of a tissue sample from a patient so that the removed tissue sample may be examined. In many cases, the histological architecture of the removed tissue is desired to be preserved for examination. Thus, a biopsy may involve not only the removal of cellular matter from a patient, but may also involve the removal of entire tissue structures. An example of a tissue structure that is sometimes removed during a biopsy is a node, such as a lymph node. Lymph nodes may be located throughout a patient's body, including in the patient's thoracic cavity. For examination purposes, a node may be removed from a patient in such a way so as to minimize any damage to the node.

Tools used for node removal, and in particularly, lymph node removal, may include node grasping clamps. One example of a node grasping clamp is a pair of DeBakey organ grasping forceps. Node grasping clamps such as the DeBakey organ grasping forceps often include a ring clamp structure that enables a practitioner to clamp a node within the ring clamp such that the node is securely held but not crushed or otherwise damaged by the clamping assembly. Instead, the clamping assembly applies pressure to the connecting tissue near the node. In the case of a lymph node, the lymph node is attached to connecting tissue via lymph ducts, which are small and easily damaged. Using the traditional DeBakey organ grasping forceps, the lymph node is secured within the ring clamp while the clamping assembly applies a clamping force to the lymph ducts which attach the lymph node to the surrounding tissue. A practitioner may then tear the lymph node from the connecting lymph ducts.

While the traditional method of lymph node removal does securely retrieve the lymph node for later examination, the mechanical tearing of the connecting lymph ducts can result in undesired side effects of the biopsy procedure. For example, torn lymph ducts typically continue to leak lymphatic fluid for many hours or even days after the lymph node is removed. The leaked lymphatic fluid may be collected and removed from the patient's body, thus resulting in additional post-operative procedures, potentially lengthening the patient's stay in a hospital, prolonging recovery and resulting in other potential complications.

Accordingly, it may be beneficial to use a node grasping clamp that reduces the amount of fluid leakage and improves patient recovery times after removal of a tissue sample, such as a node.

SUMMARY

An improved biopsy instrument for removing nodes such as lymph nodes may include one or more of a blade for mechanical cutting of the ducts that connect the node to surrounding tissue and/or an energy emitter for emitting energy to seal the ducts and/or contribute to the gentle removal of the node from its connecting ducts. The biopsy instrument may include a ring clamp assembly made up of two opposing ring structures that may be clamped together such that the desired tissue sample (e.g., a lymph node) is captured within the inside opening of the clamped rings. Connecting ducts may be severed using either a blade or energy emitted from the ring clamps. In one example, a flexible blade may be moved around the ring clamps in such a way so as to circumscribe the clamped node, cutting any connecting ducts clamped by the ring clamps. In another example, an energy emitter may be used to apply energy to the connecting ducts so as to enable the gentle removal of the node from the ducts. Energy may also be applied to the ducts in order to seal them before or after the severing of the ducts. One or more shields may also be included in the ring clamps so as to protect either the node or adjacent tissue from any adverse effects of the application of energy from the energy emitter.

In one illustrative embodiment, a biopsy instrument is described. The instrument may include a handle and a shaft extending from the handle and defining a longitudinal axis, the shaft including proximal and distal ends, the proximal end being coupled to the handle. The instrument may also include a ring clamp assembly operatively supported on the distal end of the shaft. The ring clamp assembly may include first and second ring structures, at least one of the first and second ring structures being movable to allow the first and second ring structures to open and close with respect to each other. The first and second ring structures may form a ring-shaped blade slot when in a closed position. The instrument may also include a movable cutting blade configured to move along the ring-shaped blade slot.

In an aspect, the blade slot of the biopsy instrument may be in between an inside edge and an outside edge of the closed position of the first and second ring structures. The outside edge of the closed position of the first and second ring structures may be configured to clamp tissue that traverses the blade slot. The outside edge of the closed position of the first and second ring structures may be configured to apply radio frequency (RF) energy to the clamped tissue.

In another aspect, the blade slot of the biopsy instrument may extend from the shaft and encircle the closed position of the first and second ring structures such that the blade slot includes a junction comprised of first and second ring structure blade slot portions at the distal end of the shaft. The instrument may further include a directing component at the junction that may be configured to direct the movable cutting blade to enter the first ring structure blade slot portion. The directing component may be further configured to block movement of the cutting blade from the shaft to the second ring structure blade slot portion, and to allow movement of the cutting blade from the second ring structure blade slot portion to the shaft. The directing component may be a hinged door. The directing component may also be an extension of an inside edge of the closed position of the first and second ring structures. Alternatively, the directing component is a spring.

In a second illustrative embodiment, a method of removing a node within a patient is described. The method may include clamping the node within a ring-shaped instrument, and causing a cutting blade to move along a ring-shaped blade slot in the ring-shaped instrument, whereby the node may be detached from connecting tissue via the cutting blade.

In an aspect of the method, the causing the cutting blade to move along the ring-shaped blade slot may include moving the cutting blade between an inside edge and an outside edge of the ring-shaped instrument. The method may further include using the outside edge of the ring-shaped instrument to clamp tissue that traverses the blade slot, and may also further include applying radio frequency (RF) energy to the clamped tissue via the outside edge of the ring-shaped instrument.

In another aspect of the method, the causing the cutting blade to move along the ring-shaped blade slot may include causing the cutting blade to move in a closed circular path in the ring-shaped instrument. The causing the cutting blade to move in a closed circular path in the ring-shaped instrument may include causing the cutting blade to move in a first direction around the ring-shaped instrument, the first direction resulting from a directing component located in the blade slot. Additionally, the method may further include moving the cutting blade in the first direction, past a first side of the directing component and around the ring-shaped instrument until the cutting blade returns to and passes through a second side of the directing component.

In yet another aspect of the method, the removed node may be a lymph node.

In a third illustrative embodiment, a biopsy instrument is described. The instrument may include a ring clamp assembly including first and second ring structures, at least one of the first and second ring structures being movable to allow the first and second ring structures to open and close with respect to each other. The first and second ring structures may form a ring-shaped blade slot when in a closed position. Further, a movable cutting blade may be configured to move along the ring-shaped blade slot. A radio frequency (RF) emitter may be configured to apply RF energy to tissue clamped by the ring clamp. The RF emitter may include a at least a portion of an outside edge of the closed position of the first and second ring structure.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Traditional methods of removing nodes such as lymph nodes during biopsy procedures often result in the tearing of connected ducts and the excess leakage of fluid as a result of the tearing of the ducts. When a lymph node is torn from its connecting lymph ducts, the torn ducts leak fluid and may contribute to an increased recovery time for the patient. The patient recovery time may be decreased, however, by using improved biopsy instruments as described herein.

An improved biopsy instrument for removing nodes such as lymph nodes may include one or more of a blade for mechanical cutting of the lymph ducts and/or an energy emitter for emitting energy to seal the lymph ducts and/or contribute to the gentle removal of the lymph node from its connecting lymph ducts. The biopsy instrument may include a ring clamp assembly made up of two opposing ring structures that may be clamped together such that the desired tissue sample (e.g., a lymph node) is captured within the inside opening of the clamped rings while the connecting tissue (e.g., lymph ducts) are subjected to pressure from the clamping action of the opposing ring structures. the ring clamp assembly may include a movable blade that may be moved within a blade slot located within the clamped rings of the ring clamp assembly. Thus, the movable blade may be used to surgically sever the desired tissue sample from the surrounding tissue by moving the blade along the blade slot in the ring clamp assembly. The ring clamp assembly may also include one or more energy emitters that may be used to emit energy sufficient to seal the connecting tissue. The energy emitter may be used to seal the connecting tissue either with or without the use of the movable blade. In either case, the removal of the desired tissue sample results in less fluid leakage from the connecting tissue as the connecting tissue is able to be sealed. When an energy emitter is used in the disclosed biopsy instrument, one or more energy shields may be used to protect the desired tissue sample held in the center of the ring clamp assembly from the energy released by the energy emitter. Energy emitted by the energy emitter may be used to not only seal the connecting tissue but to also weaken or otherwise prepare the connecting tissue for sample removal. The energy emitter may even facilitate cryogenic preparation of the desired tissue sample.

The following description provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in other examples.

Figure 1:
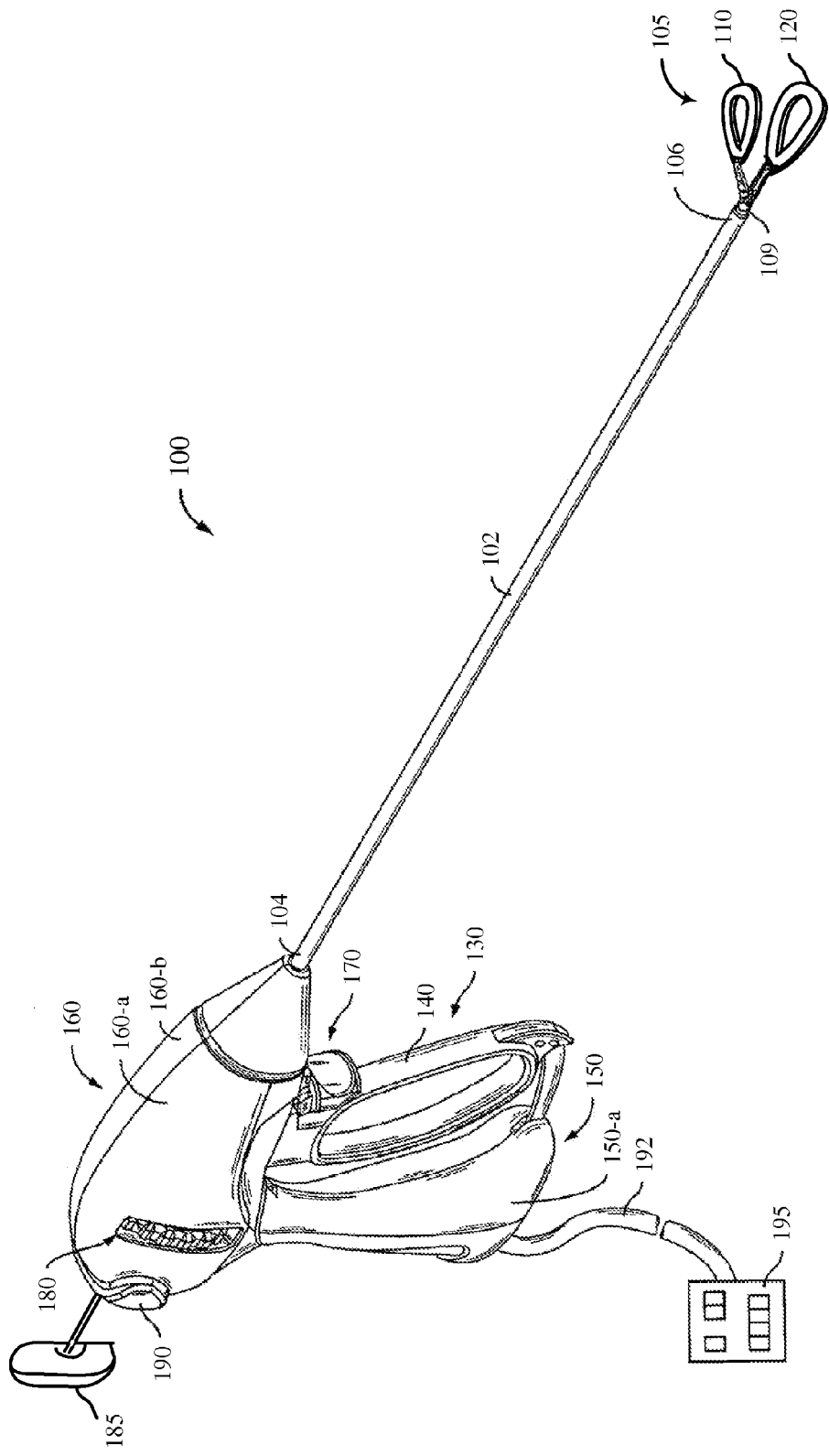
FIG. 1 shows a biopsy instrument, in accordance with various embodiments.

Referring now to the figures, FIG. 1 shows a biopsy instrument 100 for use with various endoscopic surgical procedures. The biopsy instrument 100 generally includes a housing 160, a handle assembly 130, a rotating assembly 180, a switch assembly 170 and a ring clamp assembly 105 having opposing ring clamps 110 and 120 which mutually cooperate to grasp a desired tissue sample, seal the connecting tissue to which the desired tissue sample is attached, and remove the desired tissue sample from the connecting tissue. More particularly, biopsy instrument 100 includes a shaft 102 which has a distal end 106 dimensioned to mechanically engage the ring clamp assembly 105 and a proximal end 104 which mechanically engages the housing 160. In the drawings and in the descriptions which follow, the term "proximal" refers to the end of the biopsy instrument 100 which is closer to a user of the biopsy instrument 100, while the term "distal" refers to the end which is further from the user. The shaft 102 may include one or more known mechanically engaging components which are designed to securely receive and engage the ring clamp assembly 105 such that the ring clamps 110 and 120 are pivotable relative to one another to engage and grasp tissue therebetween.

Housing 160 may include different component halves 160-a and 160-b which are assembled about the proximal end 104 of shaft 102 during assembly. Enclosed within the housing 160 is the rotating assembly 180. The rotating assembly 180 may be a gear that is manually operated to rotate the ring clamp assembly 105. To this end, shaft 102 may include a mechanism to translate the rotation of the rotating assembly 180 to the rotation of the ring clamp assembly 105.

Attached to or integral with the housing 160 is the handle assembly 130. The handle assembly 130 may include a fixed handle 150 and a movable handle 140. Fixed handle 150 may be integrally associated with the housing 160, for example, while movable handle 140 may be movable relative to the fixed handle 150, The movable handle 140 may be moved in order to actuate the opposing ring clamps 110 and 120 of the ring clamp assembly 105 as explained in more detail below.

The switch assembly 170 may be attached or adjacent to the movable handle 140. Switch assembly 170 may be configured to selectively provide electrical energy to the ring clamp assembly 105, as described in greater detail below. For example, the switch assembly 170 may enable the transmission of electrical power from the housing 160 via a cable in the shaft 102 to the ring clamp assembly 105. The switch assembly 170 and movable handle 140 may be of unitary construction and may be operatively connected to the housing 160 and the fixed handle 150 during the assembly process.

The biopsy instrument 100 may also include an electrical interface or plug 190 which connects the biopsy instrument 100 to a source of electrosurgical energy, e.g., an electrosurgical generator 195. An electrical cable 192 extends from the plug 190 and securely connects the biopsy instrument 100 to the electrosurgical generator 195. Cable 192 may also continue through the housing 160 and shaft 102 in order to transmit electrosurgical energy to the ring clamp assembly 105. Cable 192 may be internally divided within the shaft 102 to transmit electrosurgical energy through various electrical feed paths in order to facilitate the performance of different functions by the ring clamp assembly 105, as explained in greater detail below.

Ring clamp assembly 105 is attached to the distal end 106 of shaft 102 and includes the opposing ring clamps 110 and 120. Movable handle 140 of handle assembly 130 imparts movement of the ring clamps 110 and 120 from an open position wherein the ring clamps 110 and 120 are disposed in a spaced relation relative to one another, to a clamping or closed position wherein the ring clamps 110 and 120 cooperate to grasp tissue therebetween.

The ring clamps 110 and 120 are generally symmetrical and include similar component features which cooperate to permit facile rotation about pivot 109 to effect the grasping and sealing of tissue. As explained in further detail below, each ring clamp 110 and 120 includes surfaces which cooperate to engage the tissue during sealing and cutting.

Figure 2:
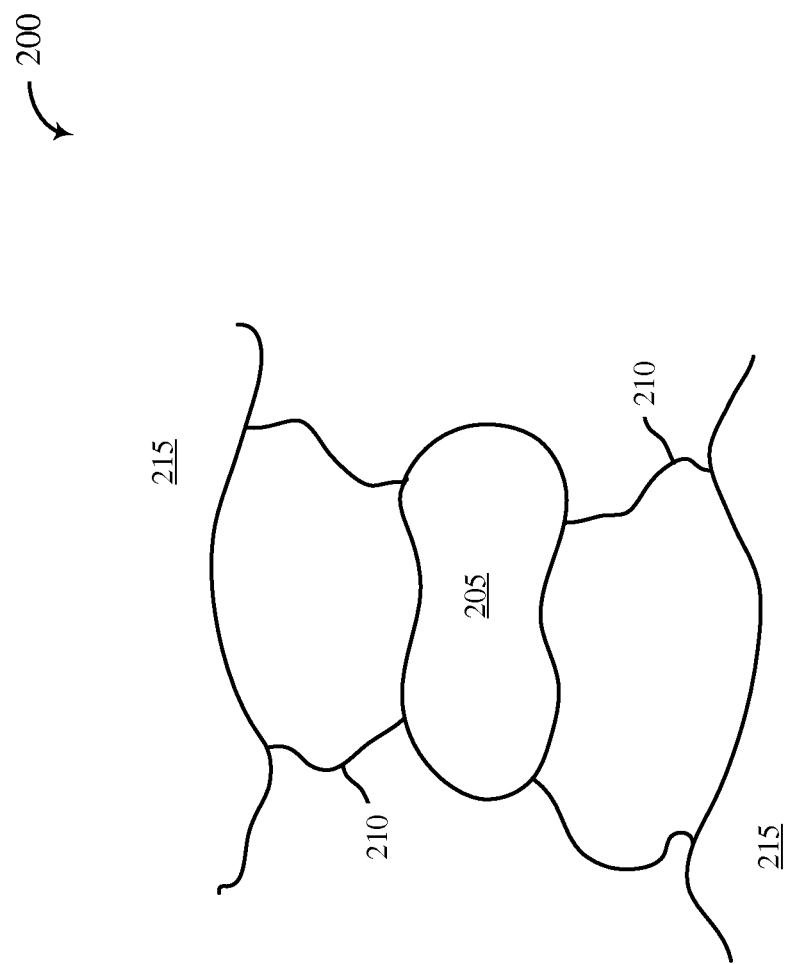
FIG. 2 shows a node that may be removed from a patient using a biopsy instrument, in accordance with various embodiments.

The biopsy instrument 100 may be used to remove nodes such as lymph nodes from a patient. FIG. 2 includes a simplified illustration 200 of a node 205 connected to surrounding tissue 215. The node 205 may be a lymph node or may be any number of similarly sized nodes. Node 205 is connected to the surrounding tissue 215 via ducts 210, such as lymph ducts. Ducts 210 may be generally thin and filament like. Thus, when nodes such as lymph nodes are removed for biopsy purposes, a tool may be used to grasp the node 205 and then tear the node 205 from the ducts 210. While such removal may not damage the node 205, the ducts 210 are damaged in such a way as to generally prolong the patient's recovery. In contrast, when biopsy instrument 100 is used to remove node 205, the connecting ducts 210 are either cut, sealed, or both so as to reduce patient recovery time.

Figure 3:
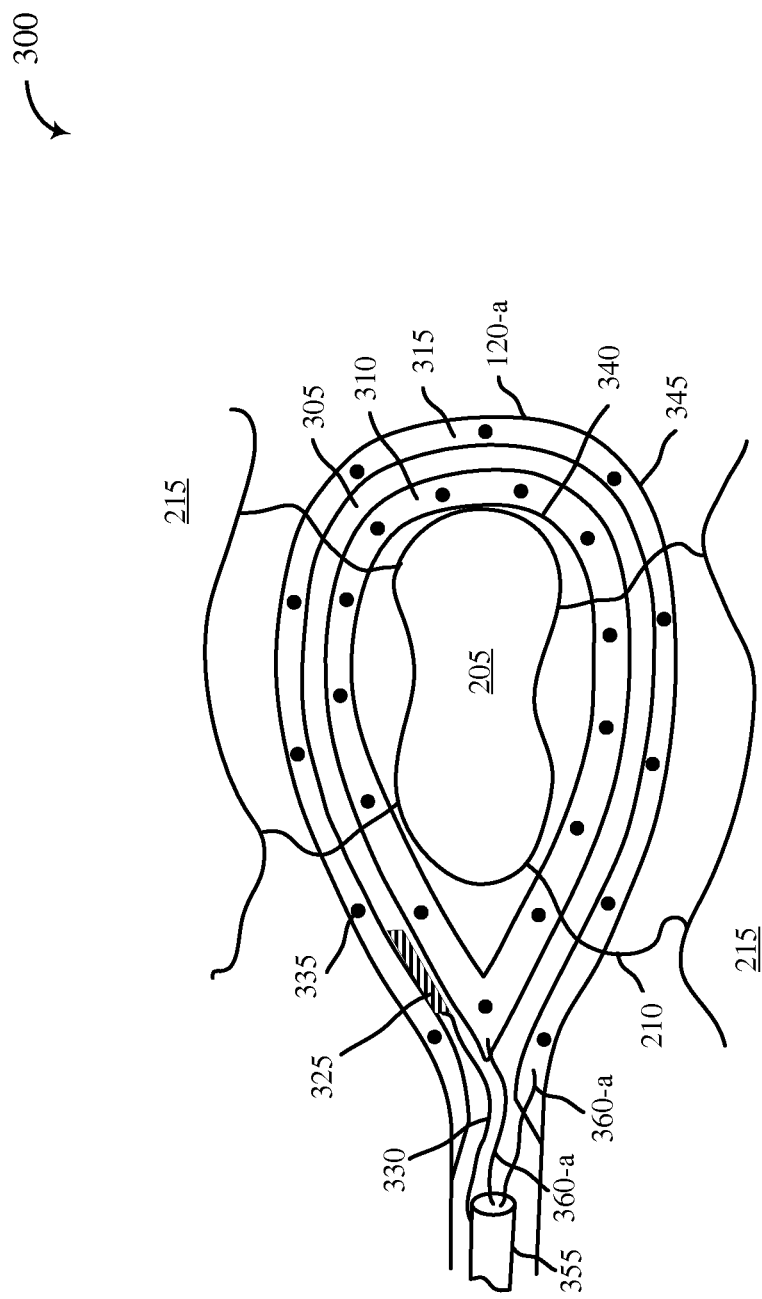
FIG. 3 shows a ring clamp of a biopsy instrument, in accordance with various embodiments.

FIG. 3 illustrates a simplified illustration 300 of ring clamp 120-a, in accordance with a disclosed embodiment. Ring clamp 120-a may be an example of ring clamp 120 of biopsy instrument 100, as illustrated in FIG. 1. Alternatively, the ring clamp shown in illustration 300 could also be an example of ring clamp 110. As shown in illustration 300, ring clamp 120-a may be used to clamp and remove a node 205 from surrounding tissue 215. In order to remove node 205, ring clamp 120-a is positioned such that node 205 rests within a central aperture of the ring clamp 120-a. The node 205 is further positioned in relation to the ring clamp 120-a such that the surrounding tissue 215 remains outside of the ring clamp 120-a. In this way, ducts 210, which connect the node 205 to the surrounding tissue 215, must necessarily traverse a portion of the ring clamp 120-a. In this way, then, ring clamp 120-a may be used to securely grasp node 205 and apply a clamping pressure to ducts 210. The clamping pressure may be provided by the closing of an opposing clamping member onto ring clamp 120-a, such as by the closing of ring clamps 110, 120 of biopsy instrument 100 (of FIG. 1).

In addition to applying pressure to the ducts 210, ring clamps 110, 120 may include additional features that may be used to surgically cut through the ducts 210 and/or seal the ducts 210. In illustration 300, ring clamp 120-a includes one or more clamping surfaces as well as a structure for cutting through the ducts 210. For example, ring clamp 120-a includes an inner clamping surface 310, an outer clamping surface 315, and a blade slot 305 in which a blade 325 may be moved. The inner clamping surface 310 may be disposed between an inner edge 340 of the ring clamp 120-a and the blade slot 305. The outer clamping surface 315 may be disposed between an outer edge 345 of the ring clamp 120-a and the blade slot 305.

The blade slot 305, which may be disposed between the inner clamping surface 310 and the outer clamping surface 315, provides a grooved path for movement of the blade 325. Although illustration 300 only shows ring clamp 120-a, an opposing ring clamp may include the same features illustrated in ring clamp 120-a. Thus, an opposing ring clamp may also include clamping surfaces and a blade slot. Thus, the blade 325 may be dimensioned such that part of the blade 325 fits within the blade slot 305 of ring clamp 120-a, while the remainder of the blade 325 may fit within a blade slot of an opposing ring clamp. The blade 325 may include a cutting edge 350 in the form of a sharpened point or in the form of a tapered or straight edge. The cutting edge 350 is located at a front edge of the blade 325 such that the blade 325 may be moved along the blade slot 305. In this way, the blade 325 may be used to slice through ducts 210 as the blade 325 is moved along the blade slot 305.

Blade 325 may be moved through the workings of a movement wire 330. Movement wire 330 may be connected to the blade 325 and may be of a sufficient stiffness to push or pull blade 325 in blade slot 305 as the movement wire 330 is itself pushed or pulled. The movement wire 330 may be included within the shaft 102 (of biopsy instrument 100 of FIG. 1) and may be controlled via operation of the blade handle 185, for example. Alternatively, the movement of the blade 325 (and movement wire 330) may be controlled by other types of mechanisms configured into housing 160 or handle assembly 130 of biopsy instrument 100, such as, for example, a trigger or additional movable handle.

Through the application of force to movement wire 330, blade 325 may be moved around some or all of the blade slot 305 in ring clamp 120-a. Thus, blade 325 and movement wire 330 is sufficiently flexible to be able to bend around the curves of the blade slot 305. When ducts 210 are positioned across the path of the blade 325, the blade 325 may be used to cut through the ducts 210.

The inner and outer clamping surfaces 310, 315, respectively, may be used to hold or clamp the ducts 210 so that they may be cut by the movement of the blade 325 in the blade slot 305. In this way, the ducts 210 may be cut cleanly instead of being torn. A clean cut can potentially heal faster.

In addition to being used to hold the ducts 210 in place, the inner and outer clamping surfaces 310, 315 may also be used to seal portions of the ducts 210 held on either side of the blade slot 305. Thus, to this end, one or both of clamping surfaces 310, 315 may be formed as a sealing plate. When clamping surfaces 310, 315 are used as sealing plates, the clamping surfaces 310, 315 may be energized via a cable 355 which may connect to or be a part of cable 192 of biopsy instrument 100 (of FIG. 1). Cable 355 may provide electrical connections to the inner and outer clamping surfaces 310, 315 via component cables 360-a, 360-b, respectively. Cable 355 may also extend through the shaft 102 of the biopsy instrument 100 in such a way as to interface with trigger assembly 170, which may be configured to switch on and off the application of electrical energy to the inner and outer clamping surfaces 310, 315.

The inner and outer clamping surfaces 310, 315, when used as sealing plates, may be configured to apply energy to portions of the ducts 210 in order to seal the ducts 210 on either side of where the ducts 210 are to be cut by blade 325. Vessel or tissue sealing is a technology which utilizes a combination of radio frequency (RF) energy, clamping pressure and precise control of gap distance (i.e., the distance between opposing ring clamps 110, 120 when closed about tissue) to effectively seal or fuse tissue between two sealing plates. Vessel or tissue sealing is more than "cauterization" which involves the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

To effectively seal tissue such as the small ducts 210 attached to node 205, controlling the gap distance between opposing sealing plates is the predominant factor. To this end, inner and outer clamping surfaces 310, 315 may include spacers 335 in the form of ceramic dots that reduce the chances of two opposing sealing plates touching each other and shorting out, while still ensuring a proper gap distance between opposing sealing plates.

One or both of the inner and outer clamping surfaces 310, 315 may be used as sealing plates. For example, in one embodiment, only the outer clamping surface 315 is used as a sealing plate. This allows the portions of the ducts 210 that remain inside a patient to be sealed without concern for sealing the portions of the ducts 210 that are removed with the node 205 during a biopsy procedure. Alternatively, both the inner and outer clamping surfaces 310, 315 may be used as sealing plates.

Figure 4:
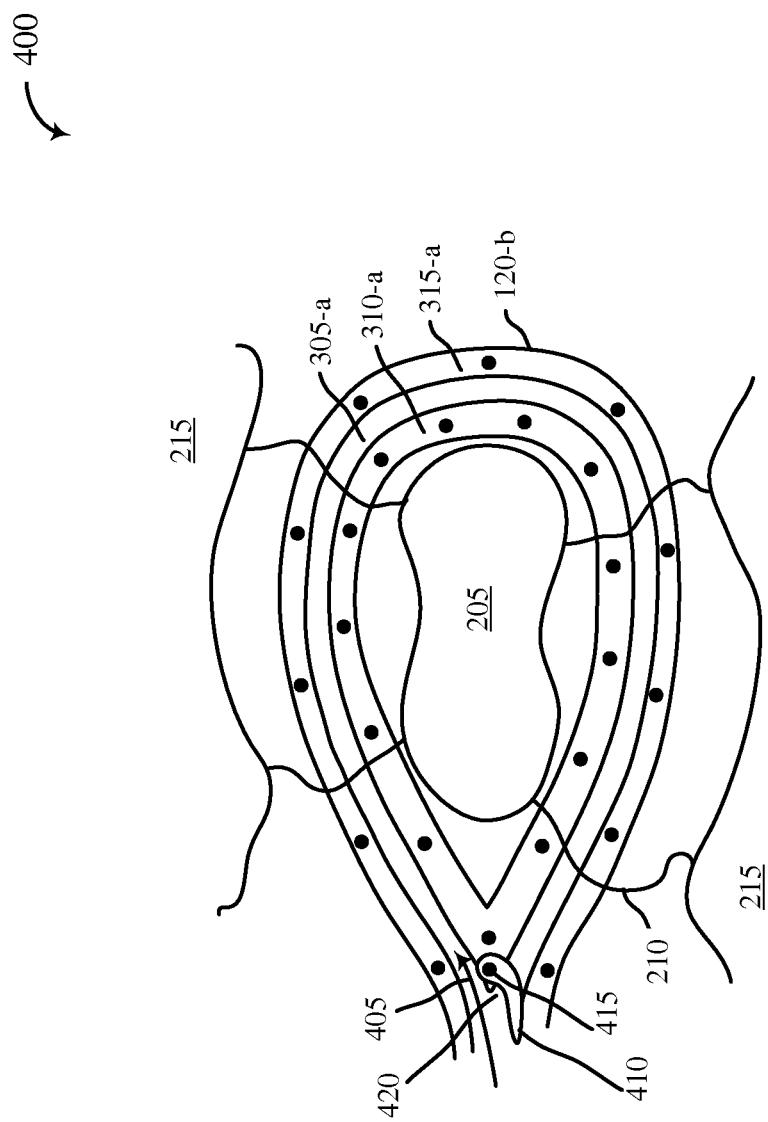
FIG. 4 shows a ring clamp of a biopsy instrument, in accordance with various embodiments.

FIG. 4 shows an illustration 400 that includes a ring clamp 120-b which may be a variation of the ring clamp 120-a described with reference to FIG. 3. In illustration 400, ring clamp 120-b may include an inner clamping surface 310-a, an outer clamping surface 315-a, and a blade slot 305-a disposed between the inner and outer clamping surfaces 310-a, 315-a. A node 205 to be removed using the biopsy instrument 100 (of FIG. 1) may be situated in the central aperture of ring clamp 120-b. Connecting ducts 210 connect the node 205 with the surrounding tissue 215.

In ring clamp 120-b, it may be desirable to control the direction of movement 405 of a blade 325 (of FIG. 3), especially at junction 420 in the blade slot 305-a, near the distal end of the shaft 102 (of FIG. 1). To this end, a directing component may be positioned at the junction 420 in order to direct the movement of the blade 325 around the blade slot 305-a. In illustration 400, the directing component may be in the form of a hinged door 410. The hinged door 410 may rotate about a spring-loaded hinge 415 located near the junction 420. The hinged door 410 may be of sufficient size so as to block passage of the blade 325 along one of the branches of the blade slot 305-a. The hinged door 410 may also be shaped such that movement of the blade 325 against the hinged door 410 will encourage the blade 325 to proceed in the direction of movement 405. For example, the hinged door 410 may be crescent-shaped. When the blade 325 is moved into the blade slot 305-a, the hinged door 410 will remain in a closed position due to the spring-loaded hinge 415. As the blade 325 is moved around the blade slot 305-a (in the direction of movement 405), the blade 325 may completely circumscribe the ring clamp 120-b and return to the opposite side of the hinged door 410. If desired, the blade 325 may be pushed with sufficient force to open the hinged door 410 such that the blade 325 may complete its movement along the blade slot 305-a. The hinged door 410 may be shaped so as to encourage the blade 325 to push open the hinged door 410 from the side of the hinged door 410 nearest the node 205. When the forward motion of the blade 325 has stopped and the blade 325 is to be retracted, the blade 325 may be pulled back through the hinged door 410, thus allowing the hinged door 410 to swing closed in response to the spring-loaded hinge 415.

Figure 5:
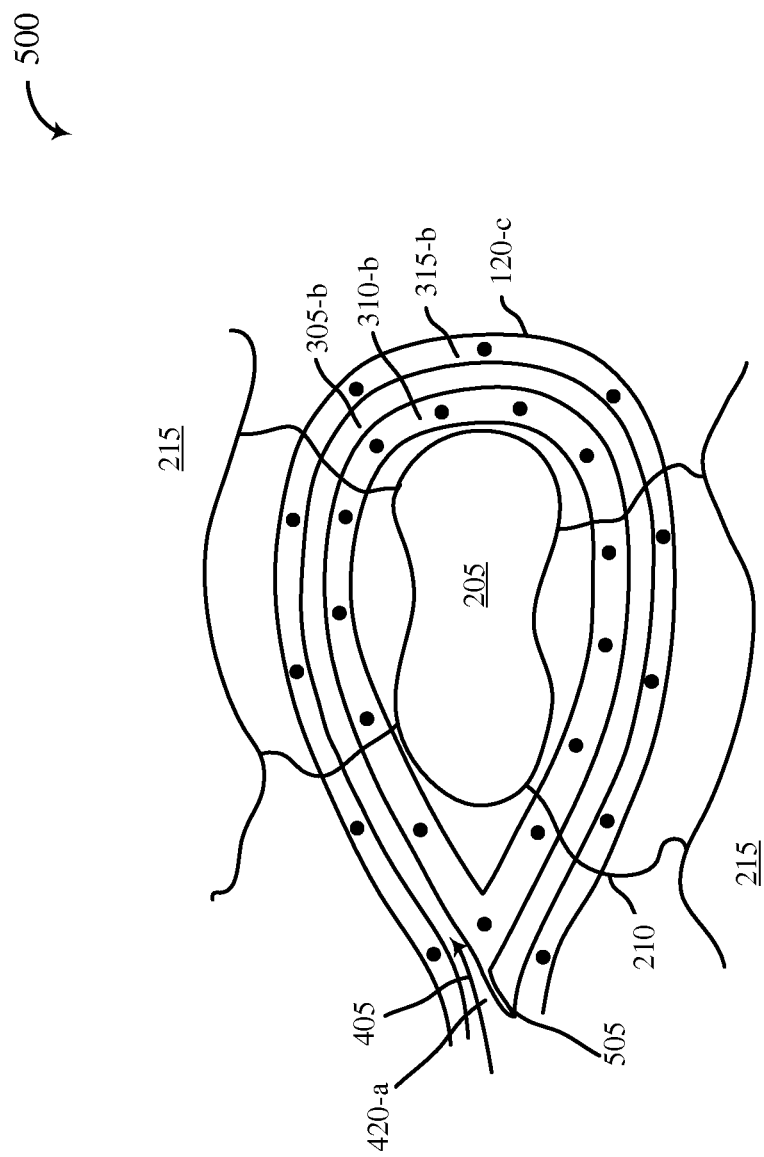
FIG. 5 shows a ring clamp of a biopsy instrument, in accordance with various embodiments.

FIG. 5 shows an additional illustration 500 that includes a ring clamp 120-c which may be yet another variation of the ring clamp 120-a described with reference to FIG. 3. In illustration 500, ring clamp 120-c may include a directing component in the form of a spring 505 such as a tensile spring. In one aspect, the spring 505 may be an extension of an inside edge or inner clamping surface 310-b of the ring clamp 120-c. Spring 505 may be located at junction 420-a and may direct the movement of blade 325 along blade slot 305-b in the direction of movement 405. The spring 505 may extend across blade slot 305-b from the inner clamping surface 310-b to the outer clamping surface 315-b when in a closed position. The spring 505 may be shaped so as to encourage movement of the blade 325 in the direction of movement 405. For example, spring 505 may be a smooth extension of the inner clamping surface such that it forms a flexible wall of the blade slot 305-b. The spring 505 remains in a closed position due to its own tensile force, but may be moved to an open position if the blade 325 applies sufficient force against the hinge 505 once the blade 325 has circumscribed the blade slot 305-b.

Figure 6:
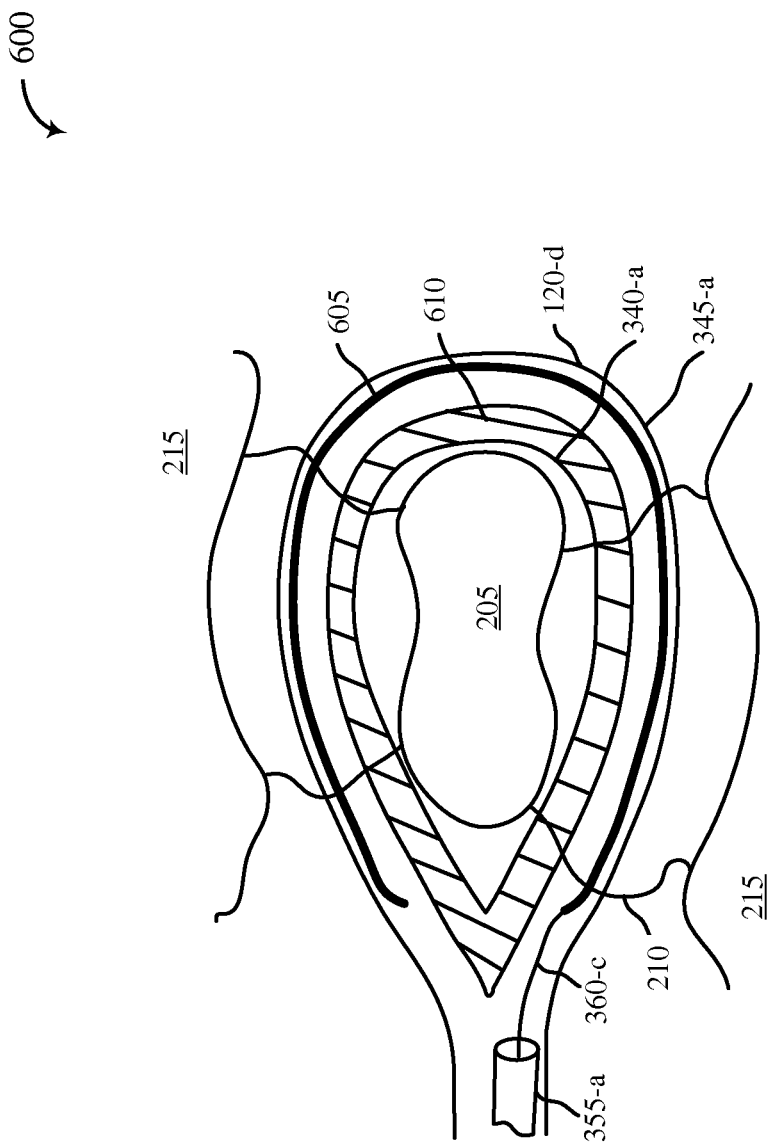
FIG. 6 shows a ring clamp of a biopsy instrument, in accordance with various embodiments.

FIG. 6 includes an illustration 600 of yet another variation of a ring clamp. In illustration 600, ring clamp 120-d may be a variation of ring clamp 120 of biopsy instrument 100 (of FIG. 1). As shown, ring clamp 120-d may be used to grasp and remove a node 205, which may be situated in the central aperture of ring clamp 120-d. Connecting ducts 210 connect the node 205 with the surrounding tissue 215.

Ring clamp 120-d may not include a blade 325 or blade slot 305 in order to cut the ducts 210. Instead, ring clamp 120-d may include an energy emitter 605 positioned along the outer edge 345-a of ring clamp 120-d. Electrical power may be provided to the energy emitter 605 via cable 355-a and component cable 360-c. Cable 355-a may be an example of cable 355 of FIG. 3 and may be part of or connect to cable 192 of biopsy instrument 100 (of FIG. 1).

The energy emitter 605 may include one or more electrodes that are configured to apply energy to the ducts 210. The purpose of the energy emitter 605 is to apply sufficient energy to the ducts 210 to allow the ducts 210 to be cut or severed in a way that reduces recovery time of a patient whose node 205 is removed. To that end, the energy emitter 605 may apply a variety of different types of energy to the ducts 210. For example, the energy emitter 605 may apply radio frequency (RF) energy to the ducts 210. The applied RF energy may be of sufficient power to heat the ducts 210 such that a gentle application of tension could sever the node 205 from the ducts 210. Similarly, microwave energy may be emitted by the energy emitter 605. Microwave energy may also be used to heat the ducts 210, allowing for gentle removal of the node 205 from the ducts 210.

Another option includes emitting ultrasonic energy. The emitted ultrasonic energy could have a sufficient strength and frequency and could be targeted to weaken the ducts 210, once again allowing for gentle removal of the node 205. Laser energy could be used to heat or to directly sever the ducts 210. In another example, cryogenic energy could be applied, effectively freezing the ducts 210, rendering them brittle and susceptible to a gentle removal of the node 205.

In each instance, the energy emitter 605 is configured to emit the desired energy in the direction of the ducts 210. In some instances, the energy emitter 605 may include components to both generate and deliver the desired energy. In other instances, the components for generating the energy may be located outside of the ring clamp 120-d (for example, within housing 160 of biopsy instrument 100 (of FIG. 1)) and the energy emitter 605 may include mechanisms to deliver the energy to the ducts 210.

The energy emitter 605 may encircle all or part of the outer edge 345-a ring clamp 120-d, and may be positioned so as to most conveniently target the ducts 210 to be cut. An opposing ring clamp may also include a symmetrically positioned energy emitter or energy emitter component that may interface with the energy emitter 605 of ring clamp 120-d.

At times, however, there may be a desire to protect the node 205 from the energy emitted by the energy emitter 605. During a biopsy procedure, for example, node 205 may need to be preserved for subsequent analysis. Therefore, to the extent that energy emitted by the energy emitter 605 might damage node 205, a shield 610 may be included in the ring clamp 120-d. The shield 610 may be positioned along the inner edge 340-a of the ring clamp 120-d and may serve to shield the node 205 from heat or other energy emitted by the energy emitter 605. The shield 610 may be made of an insulative material, for example. Thin polymer sheets, for example, may be used as the shield 610. A silicon boot may also be used as the shield 610.

Figure 7A:
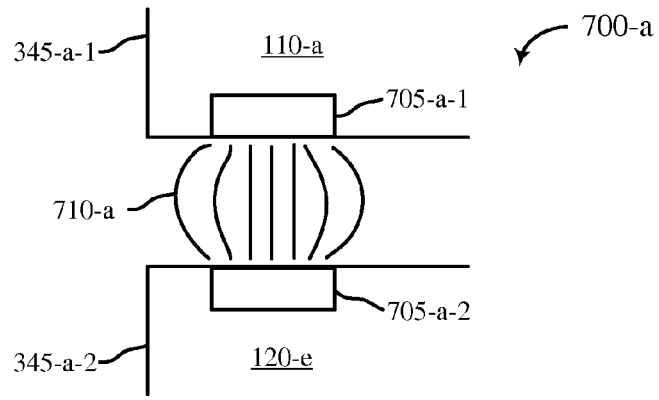
FIGS. 7A, 7B and 7C show electrode configurations on ring clamps of a biopsy instrument, in accordance with various embodiments.
Figure 7B:
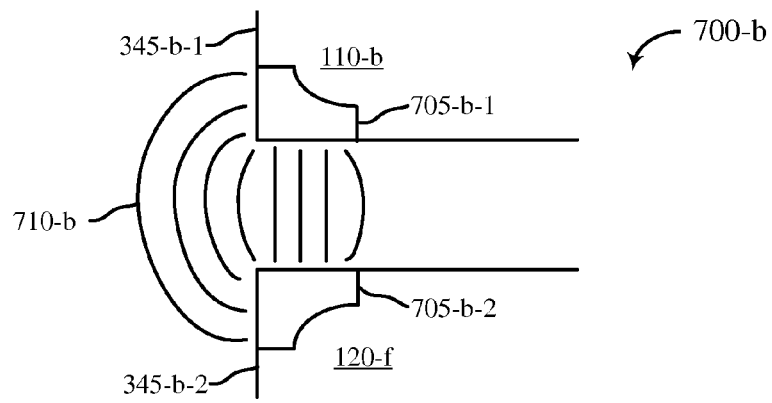
Figure 7C:
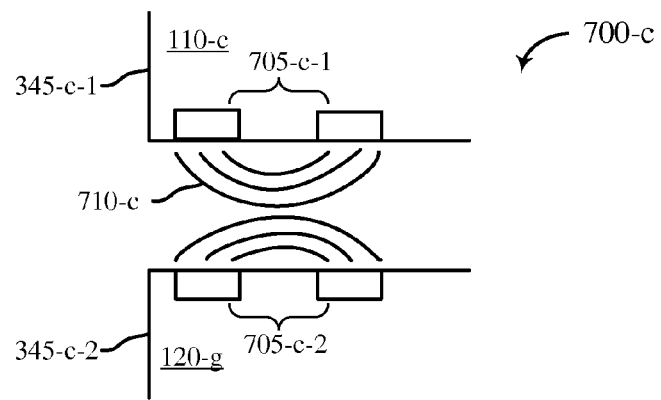

The energy emitter 605 may be configured in several different forms, as is illustrated in FIGS. 7A, 7B and 7C. FIG. 7A illustrates a diagram 700-a of a ring clamp 110-a and a ring clamp 120-e in a closed position. Ring clamp 110-a may be an example of ring clamp 110 of the biopsy instrument 100 of FIG. 1, while ring clamp 120-e may be an example of ring clamp 120 of the biopsy instrument 100 of FIG. 1. Ring clamps 110-a and 120-e may also be examples of ring clamp 120-d of FIG. 6 and other ring clamps described herein that include an energy emitter. Ring clamp 110-a includes an outer edge 345-a-1 and ring clamp 120-e includes an outer edge 345-a-2.

In diagram 700-a, ring clamp 110-a includes an electrode 705-a-1 that is opposite an electrode 705-a-2 of ring clamp 120-e. Electrodes 705-a-1 and 705-a-2 may be elements of the energy emitter 605 described in relation to ring clamp 120-d (of FIG. 6) and may be configured to emit energy at and/or through a duct 210 that may be positioned in between the electrodes 705-a-1 and 705-a-2. Electrodes 705-a-1 and 705-a-2 may be an electrode pair such that emitted energy flows between the electrodes 705-a-1, 705-a-2. Energy field 710-a is illustrated, demonstrating the energy field that may be emitted between the electrodes 705-a-1, 705-a-2 in an electrode pair. As can be seen, in the electrode configuration of diagram 700-a, an energy field 710-a may exist directly in between electrodes 705-a-1, 705-a-2. Additionally, however, the energy field 710-a may also extend outward from the edges of the electrodes 705-a-1, 705-a-2 such that structures that are not directly in between the electrodes 705-a-1, 705-a-2 may be affected by the energy field 710-a. For example, even though a node 205 may not be directly in between the electrodes 705-a-1, 705-a-2, a node 205 that is near the electrodes 705-a-1, 705-a-2 may still be affected by the energy field 710-*a*. Thus, a shield 610 (as illustrated in FIG. 6) may be useful to protect against undesired effects from the use of the energy emitter 605.

The risk of affecting a node 205 located in the central aperture of a ring clamp 120 may be lessened by both the use of a shield 610 and also the position and type of electrodes used as components of the energy emitter 605. FIG. 7B includes a diagram 700-*b* that illustrates a different electrode configuration that may further reduce the effect of emitted energy on a node 205 located in the central aperture of a ring clamp 120. For example, diagram 700-*b* illustrates a ring clamp 110-*b* and a ring clamp 120-*f* in a closed position. Ring clamp 110-*b* may be an example of ring clamp 110 of the biopsy instrument 100 of FIG. 1, while ring clamp 120-*f* may be an example of ring clamp 120 of the biopsy instrument 100 of FIG. 1. Ring clamps 110-*b* and 120-*f* may also be examples of ring clamp 120-*d* of FIG. 6 and other ring clamps described herein that include an energy emitter. Ring clamp 110-*b* includes an outer edge 345-*b*-1 and ring clamp 120-*f* includes an outer edge 345-*b*-2.

In diagram 700-*b*, ring clamp 110-*b* includes an electrode 705-*b*-1 that wraps about the outer edge 345-*b*-1 of ring clamp 110-*b*. Similarly, ring clamp 120-*f* includes an electrode 705-*b*-2 that is opposite electrode 705-*b*-1 and wraps about the outer edge 345-*b*-2 of ring clamp 120-*f*. The electrodes 705-*b*-1, 705-*b*-2 may be an electrode pair. In this electrode configuration, energy field 710-*b* is directed towards the outer edges 345-*b*-1, 345-*b*-2 of the ring clamps 110-*b*, 120-*f*. Some residual energy may still escape towards the central aperture of the ring clamps 110-*b*, 120-*f*, and thus a shield 605 may still be used to protect a node 205 being removed for biopsy (as in FIG. 6). However, the electrode configuration of diagram 700-*b* generally directs more energy away from the node 205 to be removed.

FIG. 7C includes a diagram 700-*c* that illustrates yet another electrode configuration that may further reduce the effect of emitted energy on a node 205 located in the central aperture of a ring clamp 120. In diagram 700-*c*, ring clamps 110-*c*, 120-*g* each include a pair of transverse electrodes. Specifically, ring clamp 110-*c* includes a transverse electrode pair 705-*c*-1 and ring clamp 120-*g* includes a transverse electrode pair 705-*c*-2. The transverse electrode pairs 705-*c*-1, 705-*c*-2 may be positioned near to the outer edges 345-*c*-1, 345-*c*-2 of the ring clamps 110-*c*, 120-*g*.

The energy field 710-*c* that extends from the two transverse electrode pairs 705-*c*-1, 705-*c*-2 extends in the directions of the ring clamps 110-*c*, 120-*g*, and thus further reduces the fringe energy effects that could impact a node 205 captured in the central aperture of the ring clamps 110-*c*, 120-*g*. Nevertheless, a shield 605 may still be used in order to further protect the captured node 205.

Any one of the electrode configurations illustrated in FIGS. 7A, 7B and 7C may be used in the energy emitter 605 of FIG. 6 or in other figures described below.

Figure 8:
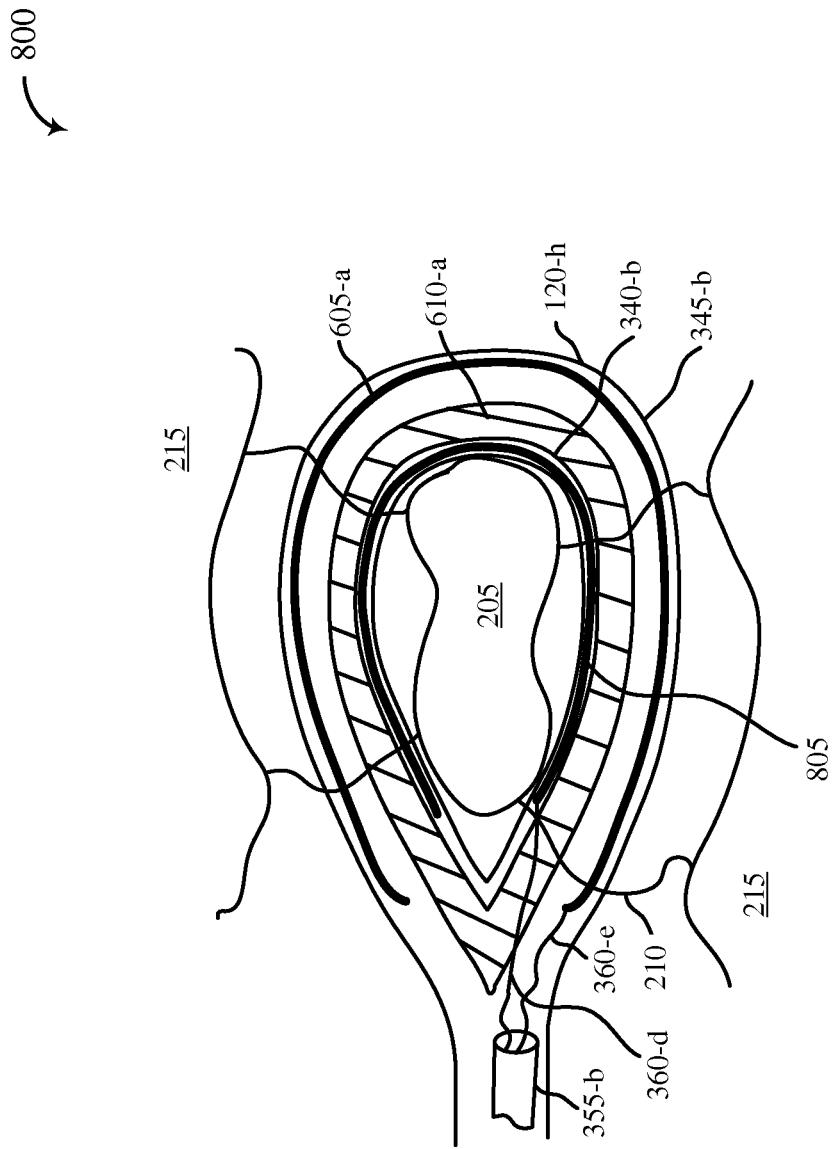
FIG. 8 shows a ring clamp of a biopsy instrument, in accordance with various embodiments.

FIG. 8 includes an illustration 800 of another variation of a ring clamp. In illustration 800, ring clamp 120-*h* may be a variation of ring clamp 120 of biopsy instrument 100 (of FIG. 1) and of ring clamp 120-*d* of FIG. 6. As shown, ring clamp 120-*h* may be used to grasp and remove a node 205, which may be situated in the central aperture of ring clamp 120-*h*. Connecting ducts 210 connect the node 205 with the surrounding tissue 215.

Ring clamp 120-*h* is similar to ring clamp 120-*d* of FIG. 6 in that it does not include a blade 325 but instead includes an energy emitter 605-*a* and a shield 610-*a*. The energy emitter 605-*a* is positioned at or near the outer edge 345-*b* of the ring clamp 120-*h*. The shield 610-*a* is disposed on the ring clamp 120-*h* in between the energy emitter 605-*a* and the inner edge 340-*b* of the ring clamp 120-*h*. The energy emitter 605-*a* and the shield 610-*a* may be examples of the energy emitter 605 and shield 610, respectively, described with reference to FIG. 6. However, in ring clamp 120-*h*, an additional cryogenic energy emitter 805 may be included in between the shield 610-*a* and the inner edge 340-*b*. Electrical power may be provided to both the energy emitter 605-*a* and the cryogenic energy emitter 805 via cable 355-*b* and component cables 360-*d*, 360-*e*. Cable 355-*b* may be an example of cable 355-*a* of FIG. 6 and may be part of or connect to cable 192 of biopsy instrument 100 (of FIG. 1).

The cryogenic energy emitter 805 may be used to apply cryogenic energy to the node 205 in preparation for its storage and analysis after the node 205 is removed from a patient. Typically, when a node 205 is removed in a biopsy procedure, the node 205 is subsequently analyzed. In order to preserve the node 205 until its analysis, the node 205 may be cryogenically frozen. Typically, the cryogenic freezing process is performed after the node 205 is removed from the patient. However, when ring clamp 120-*h* is used, the node 205 may be partially or completely cryogenically frozen even before the node 205 is removed from the patient. The cryogenic energy emitter 805 emits cryogenic energy to accomplish this.

Thus, using the ring clamp 120-*h* of FIG. 8, the node 205 may be gently removed from the ducts 210 (due to the energy applied to the ducts 210 by energy emitter 605-*a*) and either partially or completely cryogenically frozen during the removal process. The shield 610-*a* acts to both protect the node 205 from any adverse effects of the energy emitter 605-*a* and also may protect the surrounding tissue 215 from any adverse effects of the cryogenic energy emitter 805.

Figure 9:
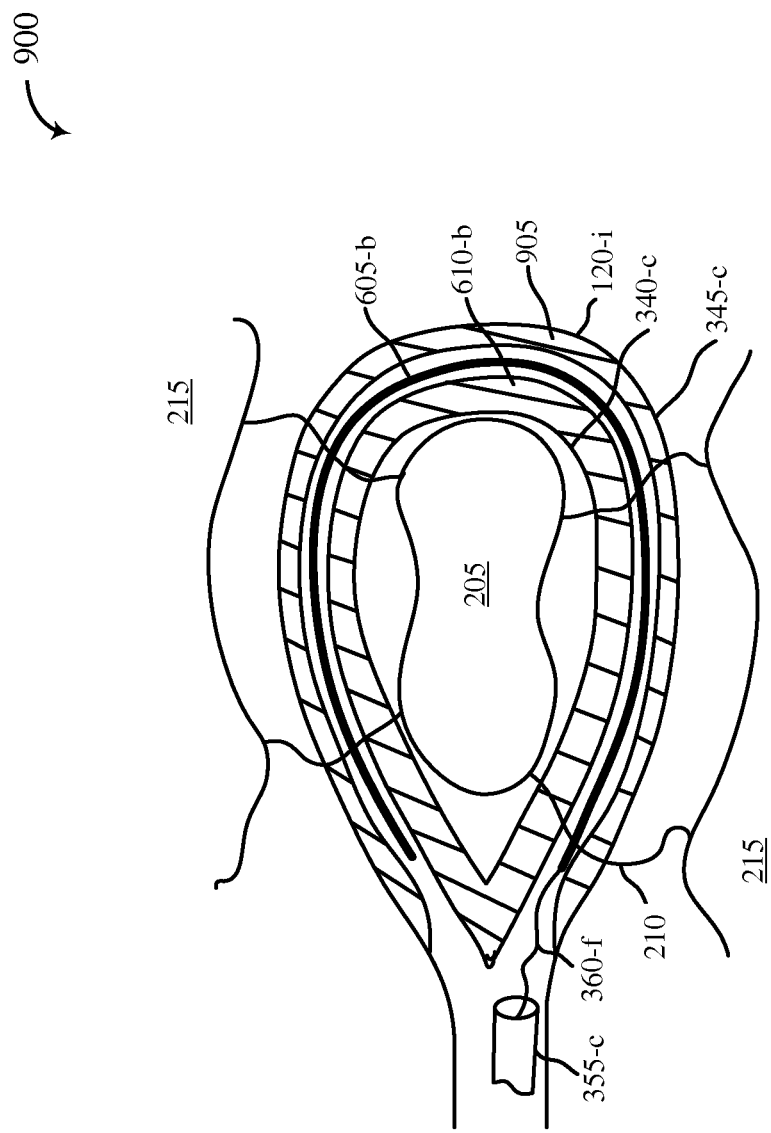
FIG. 9 shows a ring clamp of a biopsy instrument, in accordance with various embodiments.

FIG. 9 includes an illustration 900 of an additional ring clamp variation. In illustration 900, ring clamp 120-*i* may be a variation of ring clamp 120 of biopsy instrument 100 (of FIG. 1) and of ring clamp 120-*d* of FIG. 6 and/or ring clamp 120-*h* of FIG. 8. As shown, ring clamp 120-*i* may be used to grasp and remove a node 205, which may be situated in the central aperture of ring clamp 120-*i*. Connecting ducts 210 connect the node 205 with the surrounding tissue 215.

Ring clamp 120-*i* is similar to ring clamp 120-*d* of FIG. 6 in that ring clamp 120-*i* includes an energy emitter 605-*b* and a shield 610-*b*. The shield 610-*b* is disposed on the ring clamp 120-*i* in between the energy emitter 605-*b* and the inner edge 340-*c* of the ring clamp 120-*i*. The energy emitter 605-*b* and the shield 610-*b* may be examples of the energy emitter 605 and shield 610, respectively, described with reference to FIGS. 6 and/or 8. Electrical power may be provided to the energy emitter 605-*b* via cable 355-*c* and component cable 360-*f*. Cable 355-*c* may be an example of cable 355-*a* of FIG. 6 and/or cable 355-*b* of FIG. 8 and may be part of or connect to cable 192 of biopsy instrument 100 (of FIG. 1).

Ring claim 120-*i* may also include a second shield 905 located near the outer edge 345-*c* of the ring clamp 120-*i*. The second shield 905 may be used to protect the surrounding tissue 215 from any adverse effects of the energy emitted by the energy emitter 605-*b*. Thus, ring clamp 120-*i* may be used in situations where both the node 205 and the surrounding tissue 215 may have need for protection against adverse effects of the energy emitter 605-*b*. The energy emitted by the energy emitter 605-*b* may be limited in its application to only the ducts 210.

Ring clamp 120-*i* could also be combined with ring clamp 120-*h* of FIG. 8 to incorporate a cryogenic energy emitter 805 at or near the inner edge 340-*c* of the ring clamp 120-*i*, if desired.

Figure 10:
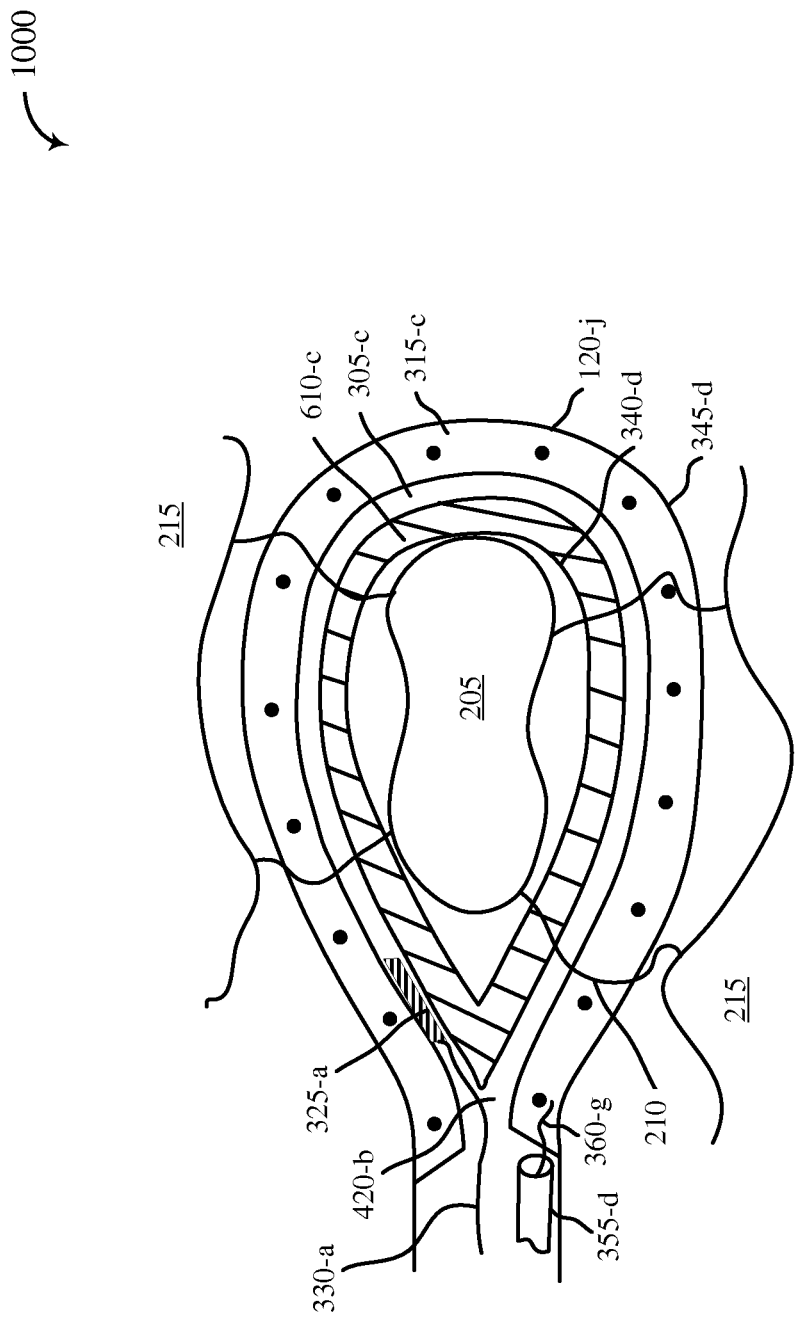
FIG. 10 shows a ring clamp of a biopsy instrument, in accordance with various embodiments.
Figure 11:
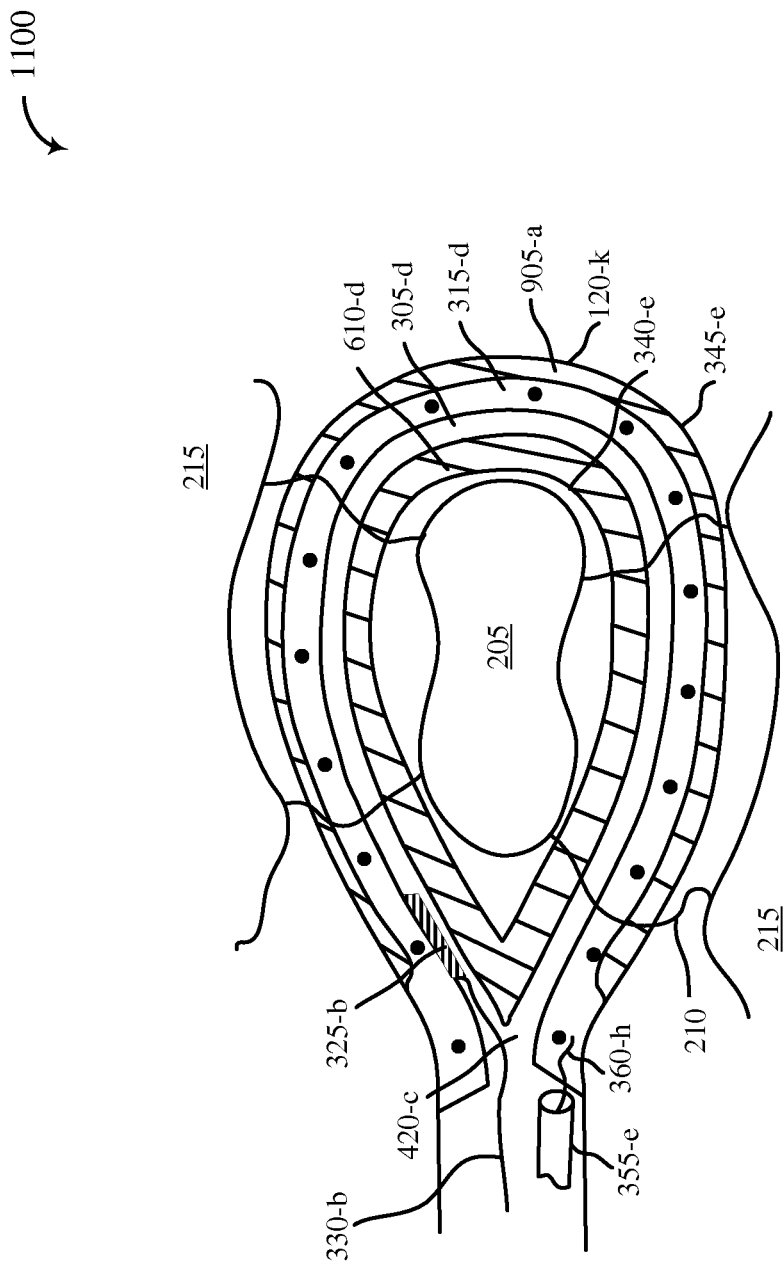
FIG. 11 shows a ring clamp of a biopsy instrument, in accordance with various embodiments.

FIGS. 10 and 11 illustrate ring clamp variations that essentially combine some of the features ring clamps incorporating a blade 325 (as shown in FIGS. 3, 4 and 5, for example) and ring clamps incorporating an energy emitter 605 (as shown in FIGS. 6, 7, 8 and 9). Although FIGS. 10 and 11 illustrate specific combinations, any combination of features identified in FIGS. 3-9 may be combined in a ring clamp.

FIG. 10 includes an illustration 1000 that shows a ring clamp 120-*j*, which may be a variation of ring clamp 120 of biopsy instrument 100 (of FIG. 1), for example. As shown, ring clamp 120-*j* may be used to grasp and remove a node 205, which may be situated in the central aperture of ring clamp 120-*j*. Connecting ducts 210 connect the node 205 with the surrounding tissue 215.

Ring clamp 120-*j* may include a clamping surface 315-*c* disposed near the outer edge 345-*d* of the ring clamp 120-*j*. The clamping surface 315-*c* may be a sealing plate and may be an example of the clamping surface 315 described with reference to FIGS. 3, 4 and/or 5. A shield 610-*c* may also be included near the inner edge 340-*d* of the ring clamp 120-*j*. The shield 610-*c* may be an example of the shield 610 described with reference to FIGS. 6, 8 and/or 9. The shield 610-*c* is disposed so as to protect node 205 from any adverse effects of the RF energy emitted by the clamping surface 315-*c*. Electrical power may be provided to the clamping surface 315-*c* via cable 355-*d* and component cable 360-*g*. Cable 355-*d* may be an example of cable 355-*a* of FIG. 6 and/or cable 355-*b* of FIG. 8 and may be part of or connect to cable 192 of biopsy instrument 100 (of FIG. 1).

Ring clamp 120-*j* may also include a blade slot 305-*c* disposed between the clamping surface 315-*c* and the shield 610-*c*. The blade slot 305-*c* facilitates movement of a blade 325-*a* around some or all of the ring clamp 120-*j*, thus cutting the ducts 210 that may traverse the ring clamp 120-*j*. Movement wire 330-*a* may be used to move the blade 325-*a* back and forth along the blade slot 305-*c*. Movement wire 330-*a* may be controlled near the proximal end 104 of the shaft 102 of the biopsy instrument 100 (of FIG. 1), as explained in relation to FIG. 3. Any of the directing components described in relation to FIGS. 4 and/or 5 may also be included at junction 420-*b*.

Therefore, ring clamp 120-*j* includes structures for sealing ducts 210, for cutting ducts 210 and for protecting the node 205 from energy emitted from the sealing plates. Although FIG. 10 only illustrates a single clamping surface 315-*c*, dual clamping surfaces may also be used, as illustrated in FIGS. 3, 4 and/or 5.

FIG. 11 includes an illustration 1100 that shows a ring clamp 120-*k*, which may be a variation of ring clamp 120 of biopsy instrument 100 (of FIG. 1), for example. As shown, ring clamp 120-*k* may be used to grasp and remove a node 205, which may be situated in the central aperture of ring clamp 120-*k*. Connecting ducts 210 connect the node 205 with the surrounding tissue 215.

Ring clamp 120-*k* is similar to ring clamp 120-*j* of FIG. 10, except that ring clamp 120-*k* also includes a second shield 905-*a* disposed near the outer edge 345-*e* of the ring clamp 120-*k*. Thus, ring clamp 120-*k* may include a shield 610-*d* near the inner edge 340-*e* of the ring clamp 120-*k*, a blade slot 305-*d*, a clamping surface 315-*d* (which may be a sealing plate), and a second shield 905-*a*. The shield 610-*d*, blade slot 305-*d*, clamping surface 315-*d* and second shield 905-*a* may each be examples of the shield 610, blade slot 305, clamping surface 315 and second shield 905, respectively, described in relation to any of FIGS. 3, 4, 5, 6, 8, 9 and/or 10. Electrical power may be provided to the clamping surface 315-*d* via cable 355-*e* and component cable 360-*h*. Cable 355-*e* may be an example of cable 355-*a* of FIG. 6 and/or cable 355-*b* of FIG. 8 and may be part of or connect to cable 192 of biopsy instrument 100 (of FIG. 1). The blade slot 305-*d* may also include a blade 325-*b* connected to a movement wire 330-*b*. Movement wire 330-*b* may be controlled near the proximal end 104 of the shaft 102 of the biopsy instrument 100 (of FIG. 1), as explained in relation to FIG. 3. Any of the directing components described in relation to FIGS. 4 and/or 5 may also be included at junction 420-*c*.

Therefore, ring clamp 120-*k* includes structures for sealing ducts 210, for cutting ducts 210 and for protecting both the node 205 and surrounding tissue 215 from energy emitted from the sealing plates. Although FIG. 11 only illustrates a single clamping surface 315-*d*, dual clamping surfaces may also be used, as illustrated in FIGS. 3, 4 and/or 5.

Figure 12:
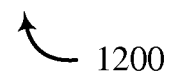
FIGS. 12-15 show flowcharts of various methods for removing a node within a patient, in accordance with various embodiments.

FIG. 12 is a flow chart illustrating an example of a method 1200 for removing a node within a patient, in accordance with various aspects of the present disclosure. For clarity, the method 1200 is described below with reference to aspects of biopsy instrument 100 described with reference to FIG. 1, as modified by ring clamps 120-*a*, 120-*b*, 120-*c*, 120-*j* and/or 120-*k* described with reference to FIGS. 3, 4, 5, 10 and/or 11.

The method 1200 may be used, for example, to remove a lymph node in a patient such that the lymph node may be later analyzed. Thus, the lymph node is removed without damage to the lymph node. Additionally, the lymph ducts are severed using a blade instead of being torn, thus reducing recovery time.

As shown in FIG. 12, at step 1205, the method 1200 includes clamping the node within a ring-shaped instrument. The ring-shaped instrument may be the biopsy instrument 100 described in relation to FIG. 1, including the ring clamps 110, 120 of biopsy instrument 100. The node may be positioned within a central aperture of the ring clamps 110, 120 when the ring clamps 110, 120 are in a closed position.

At step 1210, the method 1200 includes causing a cutting blade to move along a ring-shaped blade slot in the ring-shaped instrument, whereby the node is detached from connecting tissue via the cutting blade. This may be achieved by using a blade that is pushed and/or pulled so as to partially or fully circumscribe the clamped node positioned within the central aperture of the ring clamps 110, 120. The blade may be used to cut through the ducts that connect the clamped node with surrounding tissue.

Figure 13:
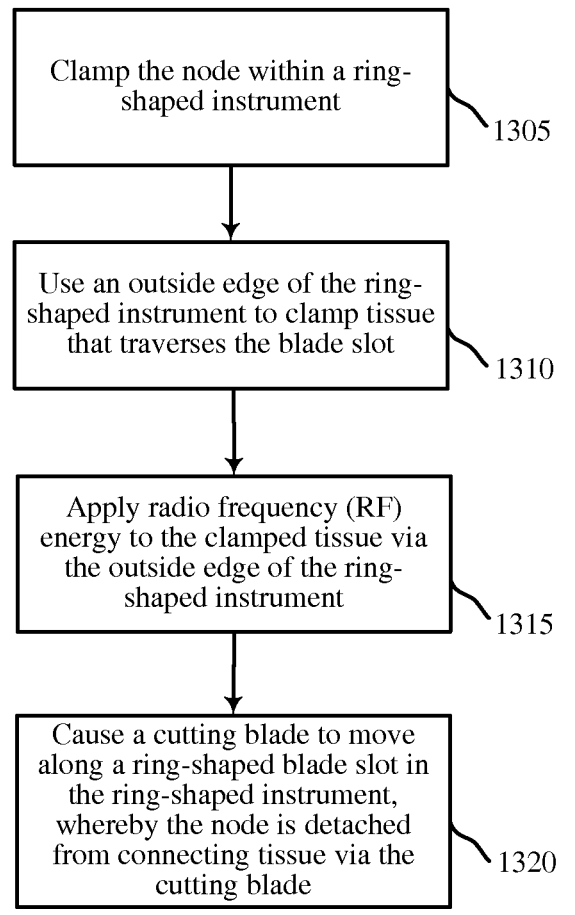

FIG. 13 is a flow chart illustrating a further example of a method 1300 for removing a node within a patient, in accordance with various aspects of the present disclosure. For clarity, the method 1300 is described below with reference to aspects of biopsy instrument 100 described with reference to FIG. 1, as modified by ring clamps 120-*a*, 120-*b*, 120-*c*, 120-*j* and/or 120-*k* described with reference to FIGS. 3, 4, 5, 10 and/or 11.

As shown in FIG. 13, at step 1305, the method 1300 includes clamping the node within a ring-shaped instrument. The ring-shaped instrument may be the biopsy instrument 100 described in relation to FIG. 1, including the ring clamps 110, 120 of biopsy instrument 100. The node may be positioned within a central aperture of the ring clamps 110, 120 when the ring clamps 110, 120 are in a closed position.

At step 1310, the method 1300 includes using an outside edge of the ring-shaped instrument to clamp tissue that traverses the blade slot. For example, the ducts that connect the clamped node with surrounding tissue may be clamped such that the ducts traverse the blade slot.

At step 1315, the method 1300 includes applying radio frequency (RF) energy to the clamped tissue via the outside edge of the ring-shaped instrument. The surface that clamps the ducts that connect the node to the surrounding tissue may also be a sealing plate and thus may be used to apply RF energy to the clamped ducts. The applied RF energy may be used to seal the ducts, either prior to or after the ducts are cut using a blade, as described below.

At step 1320, the method 1300 includes causing a cutting blade to move along a ring-shaped blade slot in the ring-shaped instrument, whereby the node is detached from connecting tissue via the cutting blade. This may be achieved by using a blade that is pushed and/or pulled so as to partially or fully circumscribe the clamped node positioned within the central aperture of the ring clamps 110, 120. The blade may be used to cut through the ducts that connect the clamped node with surrounding tissue.

Thus, using the method 1300, a node may be grasped and removed from its surrounding tissue by clamping, sealing and cutting the ducts that connect the node to the surrounding tissue.

It should be noted that method 1300 is just one implementation of a method of removing a node within a patient and that the operations of method 1300 may be rearranged or otherwise modified such that other implementations are possible.

Figure 14:
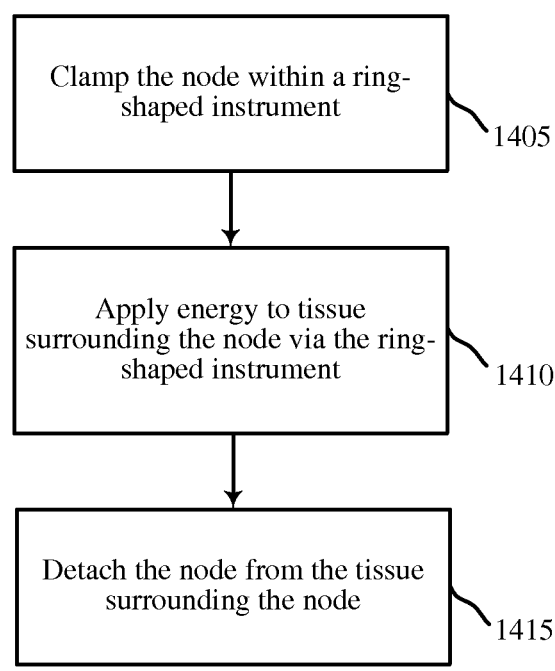

FIG. 14 is a flow chart illustrating an example of a method 1400 for removing a node within a patient, in accordance with various aspects of the present disclosure. For clarity, the method 1400 is described below with reference to aspects of biopsy instrument 100 described with reference to FIG. 1, as modified by ring clamps 120-d, 120-e, 120-f, 120-g 120-h and/or 120-i described with reference to FIGS. 6, 7A, 7B, 7C, 8 and/or 9.

The method 1400 may be used, for example, to remove a lymph node in a patient such that the lymph node may be later analyzed. Thus, the lymph node is removed without damage to the lymph node. Additionally, the lymph ducts are severed by applying energy to the ducts, thus reducing recovery time.

As shown in FIG. 14, at step 1405, the method 1400 includes clamping the node within a ring-shaped instrument. The ring-shaped instrument may be the biopsy instrument 100 described in relation to FIG. 1, including the ring clamps 110, 120 of biopsy instrument 100. The node may be positioned within a central aperture of the ring clamps 110, 120 when the ring clamps 110, 120 are in a closed position.

At step 1410, the method 1400 includes applying energy to tissue surrounding the node via the ring-shaped instrument. This may be performed by using an energy emitter that directs energy to the tissue. In particular, the energy is applied to the ducts that connect the node to other tissue. The applied energy may be in the form of radio frequency (RF) energy, microwave energy, ultrasonic energy, laser energy and/or cryogenic energy.

At step 1415, the method 1400 includes detaching the node from the tissue surrounding the node. In particular, the ducts to which the energy emitter directed its energy are weakened such that the node may be gently removed from the connecting ducts.

Figure 15:
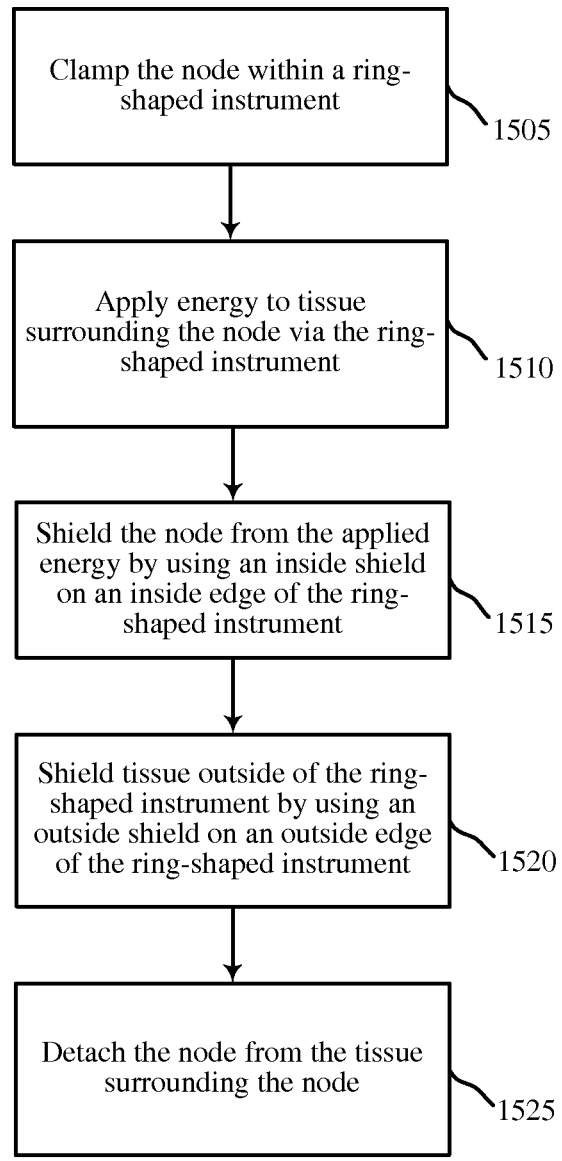

FIG. 15 is a flow chart illustrating an example of a method 1500 for removing a node within a patient, in accordance with various aspects of the present disclosure. For clarity, the method 1500 is described below with reference to aspects of biopsy instrument 100 described with reference to FIG. 1, as modified by ring clamps 120-d, 120-e, 120-f, 120-g 120-h and/or 120-i described with reference to FIGS. 6, 7A, 7B, 7C, 8 and/or 9.

As shown in FIG. 15, at step 1505, the method 1500 includes clamping the node within a ring-shaped instrument. The ring-shaped instrument may be the biopsy instrument 100 described in relation to FIG. 1, including the ring clamps 110, 120 of biopsy instrument 100. The node may be positioned within a central aperture of the ring clamps 110, 120 when the ring clamps 110, 120 are in a closed position.

At step 1510, the method 1500 includes applying energy to tissue surrounding the node via the ring-shaped instrument. This may be performed by using an energy emitter that directs energy to the tissue. In particular, the energy is applied to the ducts that connect the node to other tissue. The applied energy may be in the form of radio frequency (RF) energy, microwave energy, ultrasonic energy, laser energy and/or cryogenic energy.

At step 1515, the method 1500 includes shielding the node from the applied energy by using an inside shield on an inside edge of the ring-shaped instrument. In this way, the integrity of the node may be preserved from any adverse effects of the energy applied to the connecting ducts.

At step 1520, the method 1500 includes shielding tissue outside of the ring-shaped instrument by using an outside shield on an outside edge of the ring-shaped instrument. In this way, the integrity of any tissue surrounding the node that is not meant to be subject to the applied energy may be preserved from any adverse effects of the energy applied to the connecting ducts.

At step 1525, the method 1500 includes detaching the node from the tissue surrounding the node. In particular, the ducts to which the energy emitter directed its energy are weakened such that the node may be gently removed from the connecting ducts.

Thus, using the method 1500, a node may be grasped and removed from its surrounding tissue by clamping and applying energy to the tissue near the node (such as the connecting ducts), and then by gently removing the node from the energy-affected tissue. Shields may be used to protect tissue near the energy-affected tissue, such as the node and other tissue surrounding the node.

It should be noted that method 1500 is just one implementation of a method of removing a node within a patient and that the operations of method 1500 may be rearranged or otherwise modified such that other implementations are possible.

The above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

The detailed description set forth above in connection with the appended drawings describes exemplary embodiments and does not represent the only embodiments that may be implemented or that are within the scope of the claims. The term "exemplary" used throughout this description means "serving as an example, instance, or illustration,"

and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Features implementing functions may also be physically located at various positions, including being distributed such that portions of functions are implemented at different physical locations. Also, as used herein, including in the claims, "or" as used in a list of items indicates a disjunctive list such that, for example, a list of "at least one of A, B, or C" means A or B or C or AB or AC or BC or ABC (i.e., A and B and C).

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A biopsy instrument, comprising:
a handle;
a shaft extending from the handle and defining a longitudinal axis, the shaft including proximal and distal ends, the proximal end coupled to the handle;
a ring clamp assembly operatively supported on the distal end of the shaft, the ring clamp assembly including first and second ring structures, at least one of the first and second ring structures movable to allow the first and second ring structures to open and close with respect to each other, the first and second ring structures forming a ring-shaped blade slot when in a closed position, wherein the blade slot extends from the shaft and encircles the closed position of the first and second ring structures such that the blade slot includes a junction comprised of a first and a second ring structure blade slot portion at the distal end of the shaft; and
a movable cutting blade configured to move along the ring-shaped blade slot with respect to the first and second ring structures.

2. The biopsy instrument of claim 1, wherein the blade slot is in between an inside edge and an outside edge of the closed position of the first and second ring structures.

3. The biopsy instrument of claim 2, wherein the outside edges of the first and second ring structures in the closed position are configured to clamp tissue that traverses the blade slot.

4. The biopsy instrument of claim 1, further comprising a directing component at the junction that is configured to direct the movable cutting blade to enter the first ring structure blade slot portion.

5. The biopsy instrument of claim 4, wherein the directing component is further configured to block movement of the cutting blade from the shaft to the second ring structure blade slot portion, and to allow movement of the cutting blade from the second ring structure blade slot portion to the shaft.

6. The biopsy instrument of claim 5, wherein the directing component is a hinged door.

7. The biopsy instrument of claim 5, wherein the directing component is an extension of an inside edge of the closed position of the first and second ring structures.

8. The biopsy instrument of claim 5, wherein the directing component is a spring.

\* \* \* \* \*